(12) United States Patent
Urabe et al.

(10) Patent No.: US 8,980,919 B2
(45) Date of Patent: Mar. 17, 2015

(54) COMBINATION OF A CARBOSTYRIL AND CARNITINE

(75) Inventors: Takao Urabe, Tokyo-to (JP); Yuji Ueno, Tokyo-to (JP); Kensuke Orito, Sagamihara (JP); Hiroshi Ohno, Tokyo-to (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 358 days.

(21) Appl. No.: 12/922,414

(22) PCT Filed: Mar. 13, 2009

(86) PCT No.: PCT/JP2009/055554
§ 371 (c)(1),
(2), (4) Date: Sep. 13, 2010

(87) PCT Pub. No.: WO2009/113741
PCT Pub. Date: Sep. 17, 2009

(65) Prior Publication Data
US 2011/0015224 A1 Jan. 20, 2011

(30) Foreign Application Priority Data
Mar. 14, 2008 (JP) ................................. 2008-065448
Apr. 30, 2008 (JP) ................................. 2008-118289

(51) Int. Cl.
*A61K 31/4704* (2006.01)
*A61K 31/205* (2006.01)
*A61K 31/4709* (2006.01)

(52) U.S. Cl.
CPC ........... *A61K 31/205* (2013.01); *A61K 31/4704* (2013.01); *A61K 31/4709* (2013.01)
USPC ............ 514/314; 514/311; 514/312; 514/554

(58) Field of Classification Search
None
See application file for complete search history.

(56) References Cited

U.S. PATENT DOCUMENTS

| 4,968,719 | A | 11/1990 | Brevetti |
| 7,825,130 | B2 | 11/2010 | Hong |
| 2002/0002202 | A1 | 1/2002 | Cavazza et al. |
| 2006/0160896 | A1* | 7/2006 | Messadek ..................... 514/554 |
| 2010/0113515 | A1 | 5/2010 | Hong |

FOREIGN PATENT DOCUMENTS

| WO | WO 00/30637 | 6/2000 |
| WO | WO 01/26666 A2 | 4/2001 |
| WO | WO 2004/075897 A1 | 9/2004 |
| WO | WO 2007/032557 A1 | 3/2007 |

OTHER PUBLICATIONS

Hiatt, Medical Treatment of Peripheral Arterial Disease and Claudication, N. Engl. J. Med., vol. 344, No. 21, p. 1608-1621, May 24, 2001.*
Jacoby et al., Drug treatment of intermittent claudication, Drugs 2004: 64(15):1657-1670.*
FDA Guidance for Industry, Estimating the Maximum Safe Starting Dose in Initial Clinical Trials for Therapeutics in Adult Healthy Volunteers, Jul. 2005.*
Bristol-Meyers Squibb Co. v. Teva Pharmaceuticals, USA, Inc. (Fed. Cir., Oct. 20, 2014) (petition for rehearing en banc denied) available at http://www.cafc.uscourts.gov/images/stories/opinions-orders/13-1306.0rder. 10-16-2014.1.PDF.*
International Preliminary Report on Patentability dated Sep. 14, 2010. PCT/JP2009/055554.
Jacoby et al.; "Drug Treatment of Intermittent Claudication", Drugs, vol. 64, No. 15, pp. 1657-1670, (2004).
International Search Report from the European Patent Office for International Application No. PCT/JP2009/055554, mailing date Mar. 11, 2010.
Office Action dated Sep. 5, 2011 issued in Chinese Patent Application No. 200980117788.1.
Russian Patent Office, "Official Action," dated Feb. 25, 2013 for corresponding Russian application No. 2010141982, 12 pages.
Alyautdin, R.N., "Pharmacology," $2^{nd}$ edition, Moscow, 2004, pp. 68-73.
A.J. Liedtke et al., "Circulation Research," 1981, vol. 48, No. 6, pp. 859-866.
W. Hiatt, "Risk factor modification in intermittent claudication: effect on life expectancy and walking capacity," European Heart Journal Supplements (2002) 4 (Supplement B), B50-B54.
P. Perrone-Filardi et al., "Coronary artery disease and intermittent claudication: how to manage the patient," European Heart Journal Supplements (2002) 4 (Supplement B), B58-B62.
William R. Hiatt, "Medical Treatment of Peripheral Arterial Disease and Claudication," The New England Journal of Medicine, vol. 344, No. 21, 1608-1621, May 24, 2001.
W. R. Hiatt, "Treatment of disability in peripheral arterial disease: new drugs," Abstract of Curr Drug Targets Cardiovasac Haematol Disord. Sep. 2004; 4 (3): 227-31.
S.M. Dean, "Pharmacologic treatment for intermittent claudication," Abstract of Vasc Med. 2002; 7 (4): 301-9.
M.S. Conners et al., "Can claudication be improved with medication," Abstract of Semin Vasc Surg. Dec. 2002; 15 (4); 237-44.

(Continued)

*Primary Examiner* — Svetlana M Ivanova
(74) *Attorney, Agent, or Firm* — Finnegan, Henderson, Farabow, Garrett & Dunner, LLP

(57) ABSTRACT

The present invention relates to a medicament for treating occlusive and/or ischemic vascular disorder comprising a carbostyril derivative and carnitine.

4 Claims, 3 Drawing Sheets

(56) References Cited

OTHER PUBLICATIONS

M.R. Jaff, "Pharmacotherapy for peripheral arterial disease emerging therapeutic options," Abstract of Angiology, Nov.-Dec. 2002; 53 (6): 627-33.
S.A. Doggrell, "Pharmacotherapy of intermittent claudication," Abstract of Expert Opin Pharmacother., Nov. 2, 2001 (11): 1725-36.
R.T. Eberhardt et al., "Drug Treatment of Peripheral Vascular Disease," Abstract of Heart Dis. Jan.-Feb. 2000: (1): 62-74.
M.F. McCarty; "Hepatothemic therapy of obesity: rationale and an inventory of resources," Abstract of Med. Hypotheses Sep. 2001; 57 (3): 324-36.
M.A. Creager, "Medical Management of Peripheral Arterial Disease," Abstract of Cardiol Rev. Jul.-Aug. 2001; 9(4): 238-45.
W.R. Hiatt, "New treatment options in intermittent claudicatrion: the US experience," Abstract of Int J. Clin Pract Suppl. Apr. 2001; (119): 20-7.
W.R. Hiatt, "Current and future drug therapies for claudication," Abstract of Vasc Med 1997;2 (3): 257-62.

* cited by examiner

COMBINATION OF A CARBOSTYRIL AND CARNITINE

TECHNICAL FIELD

The present invention relates to a medicament for treating occlusive and/or ischemic vascular disorder, especially occlusive peripheral arterial disease and/or cerebrovascular accident. More particularly, it relates to a medicament for treating occlusive peripheral arterial disease and/or cerebrovascular accident which comprises a carbostyril derivative of formula (1):

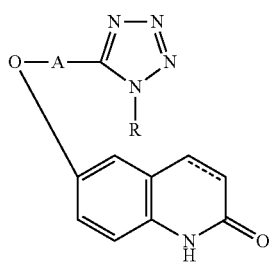

(1)

wherein A is a lower alkylene group, R is a cycloalkyl group, the bonding between 3- and 4-positions of the carbostyril skeleton is a single bond or a double bond, or a salt thereof; and carnitine or a salt thereof.

BACKGROUND ART

The carbostyril derivatives of formula (1) or salts thereof and the processes for the preparation thereof are disclosed in JP-63-20235-B and JP-55-35019-A. And it is known that the carbostyril derivatives (1) have platelet aggregation inhibition action, phosphodiesterase (PDE) inhibition action, antiulcer, hypotensive action and antiphlogistic action, and are useful as an antithrombotic agent, a drug for improving cerebral circulation, an antiinflammatory agent, an antiulcer drug, an antihypertensive drug, an antiasthmatic drug, a phosphodiesterase inhibitor, etc. A carbostyril derivative of the above formula (1), especially 6-[4-(1-cyclohexyl-1H-tetrazol-5-yl)butoxy]-3,4-dihydrocarbostyril (cilostazol) is on sale, which has an efficacy for improving various ischemic diseases such as ulcer, pain and coldness that are symptoms based on chronic arterial occlusion.

Carnitines are also called vitamin $B_T$, which are biosynthesized from essential amino acids: lysine and methionine in liver/kidney. Carnitines can penetrate a cell membrane with comparative ease and thus they are distributed to each organ and also excreted to urine. Well known carnitines are L-carnitine, carnitine chloride, levocarnitine chloride, acetylcarnitine, etc. Especially, levocarnitine chloride is on sale (commercial name: L-Cartin tablets), which has an efficacy for improving levocarnitine deficiency in propionic academia or methylmalonic acidemia, and also it is indicated that levocarnitine chloride may be useful for improving circulatory failure in lower limbs. Further, L-carnitine is also known as a food material.

Occlusive peripheral arterial disease includes acute arterial occlusive disease, thromboangiitis obliterans, arteriosclerosis obliterans, lumbar spinal stenosis, intermittent claudication and the like.

Acute arterial occlusive disease is a disease that artery is rapidly occluded for some reasons, and the symptom thereof includes sudden pain, coldness, pallor, numbness, etc.

Thromboangiitis obliterans is vasculitis in peripheral artery of extremities, especially which often happens to feet, and it is known as Buerger's disease which is chronic arterial occlusion. In addition, thromboangiitis obliterans is designated as a specific rare disease by the Japan Ministry of Health and Welfare.

Arteriosclerosis obliterans is a disease that artery of extremities is arterio-sclerosed to become stenosis/occlusion and at last circulatory deficit.

Lumbar spinal stenosis is a disease that lumbar spinal canal is constricted for some reasons and nerve tissue therein is compressed.

Intermittent claudication is the most general symptom of peripheral arterial disease, which is caused by gradually narrowing artery of feet. The symptom includes pain, cramp, and muscular lassitude, which happens in regular intervals during movement. The pain ceases when taking a break and thus it gets possible to start walking again, however, the pain happens again when walking in the same distance as walking before. Intermittent claudication may often follow from acute arterial occlusive disease, thromboangiitis obliterans, arteriosclerosis obliterans, and lumbar spinal stenosis.

The cause of cerebrovascular accident is that any trouble happens to cerebral blood vessel (blood flow), and then the subsequent hemorrhage causes inflammation/exclusion or the subsequent ischemia causes brain tissue disorder. Cerebrovascular accident includes acute cerebral infarction, chronic cerebral infarction, transient ischemic attack, intracerebral hemorrhage, subarachnoid hemorrhage, subdural hematoma, cerebrocortical dysfunction, cranial neuronal cell death, etc. And, cerebral infarction means that brain tissue is necrotized or nearly necrotized caused by occlusion/stenosis in artery and the subsequent ischemia.

DISCLOSURE OF INVENTION

As mentioned above, a carbostyril derivative of the above formula (1) (e.g. cilostazol as a typical compound) has been widely used as a medicament for treating occlusive peripheral arterial disease and a medicament for preventing the relapse of cerebral infarction, however, the present inventors have still studied for developing a more effective medicament.

The present inventors have intensively studied a new medicament thereof, and have found that a combination or a drug combination of a carbostyril derivative of the above formula (1), especially 6-[4-(1-cyclohexyl-1H-tetrazol-5-yl)butoxy]-3,4-dihydrocarbostyril (cilostazol) or a salt thereof, and carnitine or a salt thereof exhibits a dramatically potentiated action for treating occlusive peripheral arterial disease, and then have accomplished the present invention. Especially, the present inventors have found that the combination of the present invention could exhibit a more synergistically potentiated action than cilostazol as a single administration. Furthermore, it has found that the combination or the drug combination exhibits a rapid-action and a lower toxicity, thus can be administrated for a long term. Therefore, the present invention is also a useful medicament for treating peripheral arterial disease at the viewpoint of safety.

In addition, the present inventors have found that a combination or a drug combination of a carbostyril derivative of the above formula (1), especially 6-[4-(1-cyclohexyl-1H-tetrazol-5-yl)butoxyl]-3,4-dihydrocarbostyril (cilostazol) or a salt thereof, and carnitine or a salt thereof exhibits a dramatically potentiated action for treating cerebrovascular accident, and then have accomplished the present invention. The present inventors have found that the combination of the present invention could exhibit a more synergistically potentiated action than cilostazol as a single administration. Especially, it has found that the combination or the drug combination could enhance a cerebroprotective action by decreasing oxidative stress, increasing the number of oligodendrocyte cells and increasing apoptosis, and thus it can usefully act on the treatment of cerebrovascular accident. Furthermore, it has found that the combination or the drug combination exhibits a rapid-action and a lower toxicity, thus can be administrated for a long term. Therefore, the present invention is also a useful medicament for treating cerebrovascular accident at the viewpoint of safety.

In addition, the administration of a combination or a drug combination of 6-[4-(1-cyclohexyl-1H-tetrazol-5-yl)butoxy]-3,4-dihydrocarbostyril (cilostazol) or a salt thereof, and carnitine or a salt thereof has not been ever known.

The present invention provides a combination comprising as active ingredients a carbostyril derivative of the general formula:

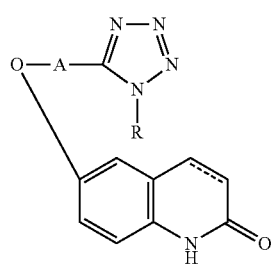

(1)

wherein A is a lower alkylene group, R is a cycloalkyl group, the bonding between 3- and 4-positions of the carbostyril skeleton is a single bond or a double bond, or a salt thereof; and carnitine or a salt thereof.

The present invention also provides a combination comprising 6-[4-(1-cyclohexyl-1H-tetrazol-5-yl)butoxy]-3,4-dihydrocarbostyril or a salt thereof, and carnitine or a salt thereof.

The present invention also provides a medicament for treating occlusive peripheral arterial disease and/or cerebrovascular accident comprising a carbostyril derivative of the general formula:

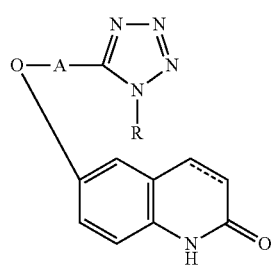

(1)

wherein A is a lower alkylene group, R is a cycloalkyl group, the bonding between 3- and 4-positions of the carbostyril skeleton is a single bond or a double bond, or a salt thereof, and carnitine or a salt thereof as active ingredients.

The present invention also provides a medicament for treating occlusive peripheral arterial disease and/or cerebrovascular accident comprising 6-[4-(1-cyclohexyl-1H-tetrazol-5-yl)butoxy]-3,4-dihydrocarbostyril or a salt thereof, and carnitine or a salt thereof as active ingredients.

The present invention provides a method for treating occlusive peripheral arterial disease and/or cerebrovascular accident comprising administering to a patient in need thereof a therapeutically effective amount of the above-mentioned combination.

The present invention provides use of the above-mentioned combination for the manufacture of the above-mentioned medicine.

In addition, the present invention also provides the above-mentioned medicament or method wherein the occlusive peripheral arterial disease is acute arterial occlusive disease, thromboangiitis obliterans, arteriosclerosis obliterans, lumbar spinal stenosis, or intermittent claudication. And, the present invention also provides the above-mentioned medicament wherein the occlusive peripheral arterial disease is intermittent claudication.

In addition, the present invention also provides the above-mentioned medicament or method wherein the cerebrovascular accident is acute cerebral infarction, chronic cerebral infarction, transient ischemic attack, intracerebral hemorrhage, subarachnoid hemorrhage, subdural hematoma, cerebrocortical dysfunction, or cranial neuronal cell death.

The present invention provides a composition for treating peripheral arterial disease and/or cerebrovascular accident comprising the combination.

According to the present invention, the combination of the carbostyril derivative (1), especially 6-[4-(1-cyclohexyl-1H-tetrazol-5-yl)butoxyl]-3,4-dihydrocarbostyril or a salt thereof, and carnitine or a salt thereof exhibits effective therapeutic and prophylactic actions for peripheral arterial disease, and effective therapeutic, prophylactic and secondary preventive actions for cerebrovascular accident, and thus has a wide-action of cerebroprotection.

BEST MODE FOR CARRYING OUT THE INVENTION

Figure 1:
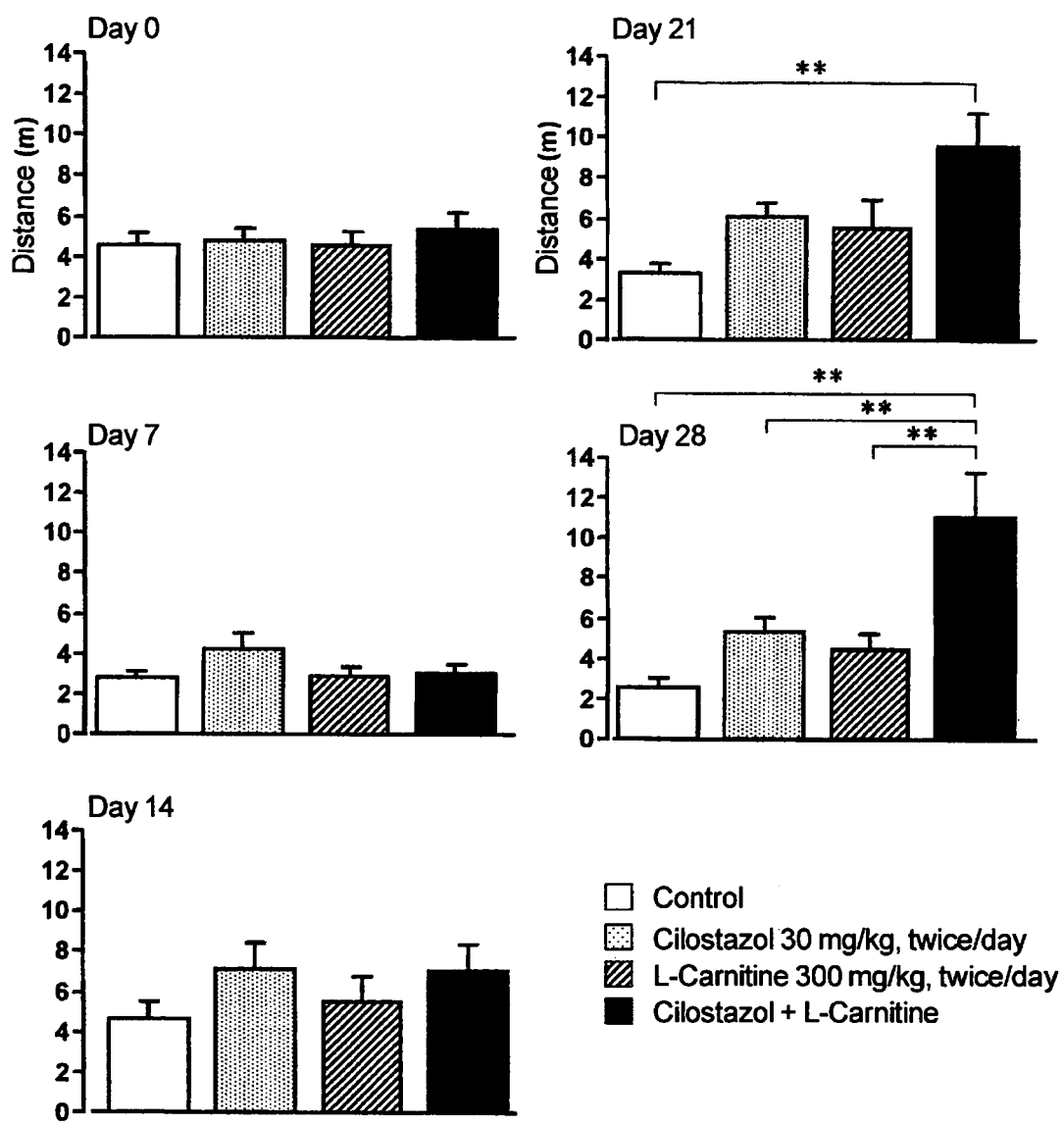
FIG. 1 shows each distance which the rats just before starting the multiple-administration (day 0) and the rats of days 7, 14, 21 and 28 after starting the multiple-administration ran on the treadmill before taking on any gait disturbance, which was affected by the administration of cilostazol, L-carnitine and the combination thereof. The mark ** means significant difference under the Bonferroni multiple comparison ($<0.01$).

The carbostyril derivative which is comprised in the drug combination or is used as the combination with carnitine or a salt thereof is a tetrazolylalkoxy-dihydrocarbostyril derivative of the formula:

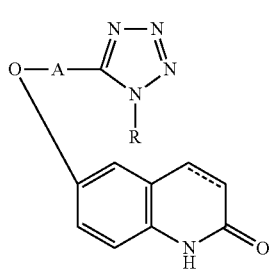

(1)

wherein A is a lower alkylene group, R is a cycloalkyl group, the bonding between 3- and 4-positions of the carbostyril skeleton is a single bond or a double bond, or a salt thereof.

In the above formula (1), the cycloalkyl group includes $C_3$-$C_8$ cycloalkyl groups such as cyclopropyl, cyclobutyl, cyclopentyl, cyclohexyl, cycloheptyl, and cyclooctyl. Preferred cycloalkyl group is cyclohexyl. The lower alkylene group includes $C_1$-$C_6$ alkylene groups such as methylene, ethylene, propylene, tetramethylene, butylene, and pentylene, among which preferred one is tetramethylene.

Preferable carbostyril derivative is 6-[4-(1-cyclohexyl-1H-tetrazol-5-yl)butoxy]-3,4-dihydrocarbostyril, which has been put on the market in the trade name of cilostazol as an antiplatelet agent.

The carbostyril derivative (1) can be easily converted to a salt thereof by getting it treated with a pharmaceutically acceptable acid. The acid includes, for example, inorganic acids such as hydrochloric acid, sulfuric acid, phosphoric acid, and hydrobromic acid; and organic acids such as oxalic acid, maleic acid, fumaric acid, malic acid, tartaric acid, citric acid, and benzoic acid.

These carbostyril derivatives (1) and salts thereof and processes for preparation thereof are disclosed in JP-55-35019-A (relevant to U.S. Pat. No. 4,277,479).

The carnitine which is the other active ingredient includes L-carnitine, carnitine chloride, levocarnitine chloride, acetyl-carnitine and the like, especially L-carnitine and levocarnitine chloride are preferable. The carnitine of the present invention can be easily transformed into a salt form by treating with a pharmaceutically acceptable acid. The acid includes, for example, inorganic acids such as hydrochloric acid, sulfuric acid, phosphoric acid, and hydrobromic acid; and organic acids such as oxalic acid, maleic acid, fumaric acid, malic acid, tartaric acid, citric acid, and benzoic acid.

These active ingredients: the carbostyril derivative (1) or a salt thereof and carnitine or a salt thereof may be administered together or separately, at the same time or different time. These ingredients may usually be used in a conventional pharmaceutical formulation. Then, these ingredients may be prepared in a single dosage form or in separate dosage forms.

The medicament of the present invention comprising a carbostyril derivative of the above formula (1) or a salt thereof, and carnitine or a salt thereof exhibits a useful therapeutic effect for occlusive peripheral arterial disease, for example, acute arterial occlusive disease, thromboangiitis obliterans, arteriosclerosis obliterans, lumbar spinal stenosis, intermittent claudication, and the like, and especially exhibits an effective action for intermittent claudication.

The medicament of the present invention comprising a carbostyril derivative of the above formula (1) or a salt thereof, and carnitine or a salt thereof also exhibits a useful therapeutic effect for cerebrovascular accident, for example, acute cerebral infarction, chronic cerebral infarction, transient ischemic attack, intracerebral hemorrhage, subarachnoid hemorrhage, subdural hematoma, cerebrocortical dysfunction, or cranial neuronal cell death, and thus has a wide-action of cerebroprotective.

Cerebrovascular accident includes acute cerebral infarction, chronic cerebral infarction, transient ischemic attack, intracerebral hemorrhage, subarachnoid hemorrhage, subdural hematoma, cerebrocortical dysfunction, cranial neuronal cell death, and the like. Cerebral infarction means a necrosis or a necrotizing condition of brain tissue via occlusion/stenosis of artery followed by ischemia. The acute phase of cerebral infarction sets up the most severe symptom, and there is a report that the prevention of free radical may act on the improvement of prognosis thereof. And the relapse probability of a person who suffered from cerebral infarction before is high. Transient ischemic attack is an attack which is transiently developing a local manifestation of brain because of the cardiovascular abnormality of brain, and the symptom thereof can often recover in a few minutes to a few hours. Intracerebral hemorrhage means a condition of bleeding in brain caused by a vascular break for some reasons. Subarachnoid hemorrhage is caused by hemorrhage into cerebrospinal fluid, and it is a disease of very high mortality. Subdural hematoma means a hematoma caused by accumulating blood in a gap between brain and a membrane of dura mater which laps brain in a cranial bone. Cerebrocortical dysfunction causes a dysfunction of cerebral cortex and then it may develop dementia or cognitive impairment. The cause of cranial neuronal cell death includes amyotrophic lateral sclerosis (ALS), Parkinson's disease, age-related cerebral dysfunction such as Alzheimer's disease and senile memory impairment, as well as cranial neuronal cell death arising in the prognosis of ischemic brain dysfunction such as cerebral infarction.

The dose of these active ingredients is not limited to a specific range. The carbostyril derivatives (1) or a salt thereof may be used in an amount of 50 to 200 mg/day per an adult (50 kg of body weight), which is administered once a day or two to several times per day. Carnitine may be used in an amount of 500 to 1000 mg/day per an adult (50 kg of body weight), which is usually administered one to three times per day. When these ingredients are prepared in a single dosage form, they are incorporated in a ratio of 0.1 to 100 parts by weight, preferably 1 to 20 parts by weight of carnitine per 1 part by weight of the carbostyril derivative (1) or a salt thereof. And, the drug combination may include the sum of the ingredients in 0.1-70% (w/w) per the preparation, but not limited thereto.

The each dosage form used for the drug combination or the combination in the present invention includes, for example, the dosage forms exemplified in JP-10-175864-A, and typically an oral solid dosage form such as tablets and capsules, an oral liquid dosage form such as syrups and elixirs, a parenteral dosage form such as injections, and an inhalant.

The preparations of the invention such as tablets, capsules, liquid for oral administration may be prepared by a conventional method. The tablets may be prepared by mixing the active ingredient(s) with conventional pharmaceutical carriers such as gelatin, starches, lactose, magnesium stearate, talc, gum arabic, and the like. The capsules may be prepared by mixing the active ingredient(s) with inert pharmaceutical fillers or diluents and filling hard gelatin capsules or soft capsules with the mixture. The oral liquid preparations such as syrups or elixirs are prepared by mixing the active ingredient(s) with sweetening agents (e.g. sucrose), preservatives (e.g. methylparaben, propylparaben), colorants, flavors, and the like. The preparations for parenteral administration may also be prepared by a conventional method, for example, by dissolving the active ingredient(s) of the present invention in a sterilized aqueous carrier, preferably water or a saline solution. Preferred liquid preparation suitable for parenteral administration is prepared by dissolving the daily dose of the active ingredients as mentioned above in water and an organic solvent and further in a polyethylene glycol having a molecular weight of 300 to 5000, in which preferably a lubricant such as sodium carboxymethylcellulose, methylcellulose, polyvinyl-pyrrolidone, and polyvinyl alcohol is incorporated. Preferably, the above liquid preparations may further comprise a disinfectant (e.g. benzyl alcohol, phenol, thimerosal), a fungicide, and further optionally an isotonic agent (e.g. sucrose, sodium chloride), a topical anesthetic, a stabilizer, a buffer, and the like. In view of keeping stability, the preparation for parenteral administration may be put in capsules, followed by removing the aqueous medium by a conventional lyophilizing technique. The preparation can be recovered into a liquid preparation by dissolving in an aqueous medium when used. The inhalants may be prepared by a conventional method. That is, the inhalants may be prepared by getting an active compound to a powder or liquid state, mixing it into propellants and/or carriers for inhalant, and charging an appropriate vaporizer with the mixture. Ordinarily, a mechanical powder vaporizer can be used when the active compound is a powder, and a vaporizer such as a nebulizer can be used when the compound is a liquid. In addition, the inhalant may optionally comprise a surfactant, an oil, a flavor, a cyclodextrin or a derivative thereof which has been used when necessary.

The examples of the above-mentioned additive agents, processes thereof, or other things include, but not limited thereto, what JP-10-175864-A discloses.

EXAMPLE

Improvement Effect for Circulatory Failure in Lower Limbs of an Intermittent Claudication Rat Model with the Combination of Cilostazol and L-Carnitine The improvement effect for circulatory failure in lower limbs with the combination of cilostazol and L-carnitine was studied through a gain improvement effect on intermittent claudication model rats as an indicator, compared with each single administration of both the medicaments.

Method (1) Preparation of a Drug Solution

Cilostazol provided by Otsuka Pharmaceutical was suspended in 5%, gum arabic so that the concentration thereof should be 6 mg/ml: and then the cilostazol suspension was administered in an amount of 5 ml/kg to the rats. L-carnitine HCl (Sigma) was dissolved in purified water so that the concentration thereof should be 300 mg/ml, and then the L-carnitine solution was administered in an amount of 1 ml/kg to the rats.

(2) Treadmill Run Test

The experimental procedure was carried out according to the method of Orito et al. (J Pharmacol Toxicol Methods 49, 25-29, 2004). That is, male SD rats (aged 9 weeks, SLC) were trained for 4 days so that they could continuously run on the treadmill. On day 6, the abdominal cavity thereof was opened under etherization and the left iliac artery was ligated at the distal portion. Three days after the ligation, the rats were made to run on the treadmill for 4 days and then the distance which the rats ran before taking on any gait disturbance was measured. Based on the data on the last day (4th day) when the rats had been made to run on the treadmill, the rats were divided into the following four groups in a random manner. To the rats in each group, each defined multiple-administration was done. The number of the experimental rats was nine per a group.

The 1st group: oral administration (twice/day) of 5% gum arabic, 5 ml/kg (control).

The 2nd group: oral administration (twice/day) of cilostazol, 30 mg/kg.

The 3rd group: oral administration (twice/day) of L-carnitine, 300 mg/kg.

The 4th group: oral administration (twice/day) of cilostazol, 30 mg/kg+L-carnitine, 300 mg/kg.

Three days after starting the administration, the treadmill test was continuously carried out for 5 days, and subsequently, only the administration was done for 2 days. Further, after that, the administration and the treadmill test (continuous 5 days)+only the administration (continuous 2 days) were repeated. In the end, the run was done for 4 weeks in total. The treadmill test was done about one hour after the administration, and the distance which the rats ran on the treadmill before taking on any gait disturbance was measured.

Statistics

Using the rats just before starting the multiple administration (day 0) and the rats of days 7, 14, 21 and 28 after starting the multiple administration, the distance which the rats ran before taking on any gait disturbance was measured and the results was analyzed about the difference between each group according to the Bonferroni multiple comparison. It was estimated by $P<0.05$ that the results exhibited significant.

Result and Consideration

With regard to the rats of days 0, 7 and 14, there was no significant difference between each group. However, on day 21, the distance which the rats in the cilostazol+L-carnitine combination group ran before taking on any gait disturbance significantly increased compared with the control group (FIG. 1). In addition, on day 28 after starting the multiple-administration, the distance of the combination group significantly increased compared with not only the control group, but also the cilostazol single group and the L-carnitine single group (FIG. 1).

The above results suggested that the combination of cilostazol and L-carnitine could intensify the improving effect for ischemia on/after day 21 at least, compared with the single administration of cilostazol.

It is thought that intermittent claudication is caused by combining a metabolic abnormality of lower limb muscle and ischemia. From the experimental results, carnitine exhibited the effect for the former, i.e. a metabolic abnormality of lower limb muscle, while cilostazol exhibited the effect for the latter, i.e. ischemia. Therefore, it is thought that the combination of these two medicaments provided a synergistic effect for intermittent claudication. It is particularly worth noting that the effect is a synergistic improving effect which is gained after a long-term administration, and additionally the effect is very potent and far more than the expected effect.

Study about Cerebroprotective Action with Cilostazol Using Chronic Ischemia Model Animals The cerebroprotective action of cilostazol for inflammatory reaction due to oxidative stress and glial cell was studied using chronic cerebral ischemia model rats as cerebrovascular dementia model animals.

Method

Using Wister rats (male, aged 7-8 weeks, body weights of 150-200 g), chronic cerebral ischemia model rats are prepared according to the method of Wakita et al. (Acta Neuropathol (Berl). 87, 484-492, 1993), i.e. by double-ligating both internal carotid arteries of the rats. As a physiological evaluation, body temperature and body fluid of the rats before/after the preparation are measured, and the cerebral blood flow thereof is analyzed with a Doppler device. To the rats of each administration group of vehicle, L-carnitine, cilostazol, and L-carnitine/cilostazol combination, each defined administration is done every day by natural ingestion from the day when the preparation of ischemia was completed to the final day for the experimental evaluation. On days 7, 14, 21 and 30 after the onset of ischemia, the rats of each administration group are perfusion-fixed with 4% PFA, and are histopathologically (immunohistologically) evaluated. After brain parenchyma of the rats is sliced in 20 μm, HE and KB stainings and several immunostainings are carried out. The dosage of each trial is 600 mg/kg/day for L-carnitine and 50 mg/kg/day for cilostazol.

Regarding glial cell, the astrocyte is evaluated with an antibody for GFAP, the microglia is evaluated with an antibody for Iba-1, and the oligodendrocyte is evaluated with an antibody for glutathione S-transferase p$^+$ (GST-pi). And, the oxidative stress is evaluated with an antibody for anti 4-hydroxy-2-nonenal (HNE).

The evaluation of each group is carried out by the method of Morris (227. R. G. M. Morris, Spatial localization does not require the presence of local cues. Learn. Motiv. 12 pp. 239-260, (1981)) which is a method for measuring memory learning of spatial recognition.

Result

Figure 2:
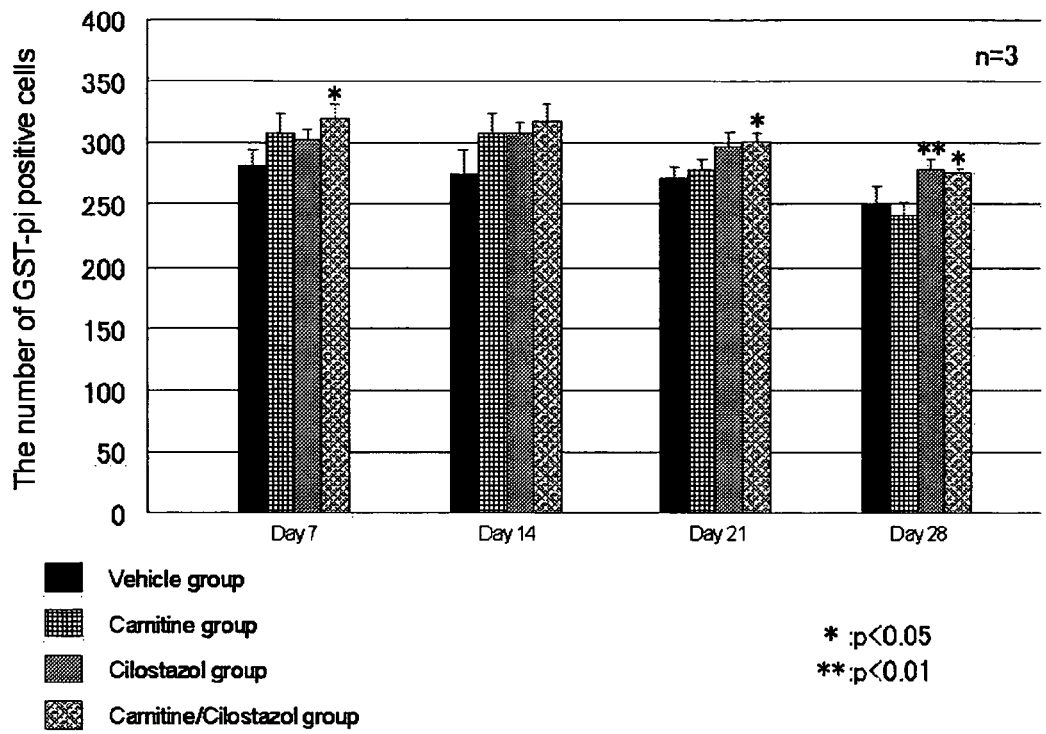
FIG. 2 shows the time-dependent change of the number of GST-pi positive cells (GST-pi staining: 0.25 cm$^2$) in each group.

As shown in FIG. 2, GST-pi positive oligodendrocyte in the callosum tended to increase from day 7 to day 14 after the ligation of both common carotid arteries (LBCCA), and it decreased after day 14. The number of the oligodendrocyte in the administration groups of carnitine and cilostazol increased more than that of the vehicle group, especially the carnitine/cilostazol combination group exhibited significant difference for the vehicle group on days 7 and 21 (P<0.05).

Figure 3:
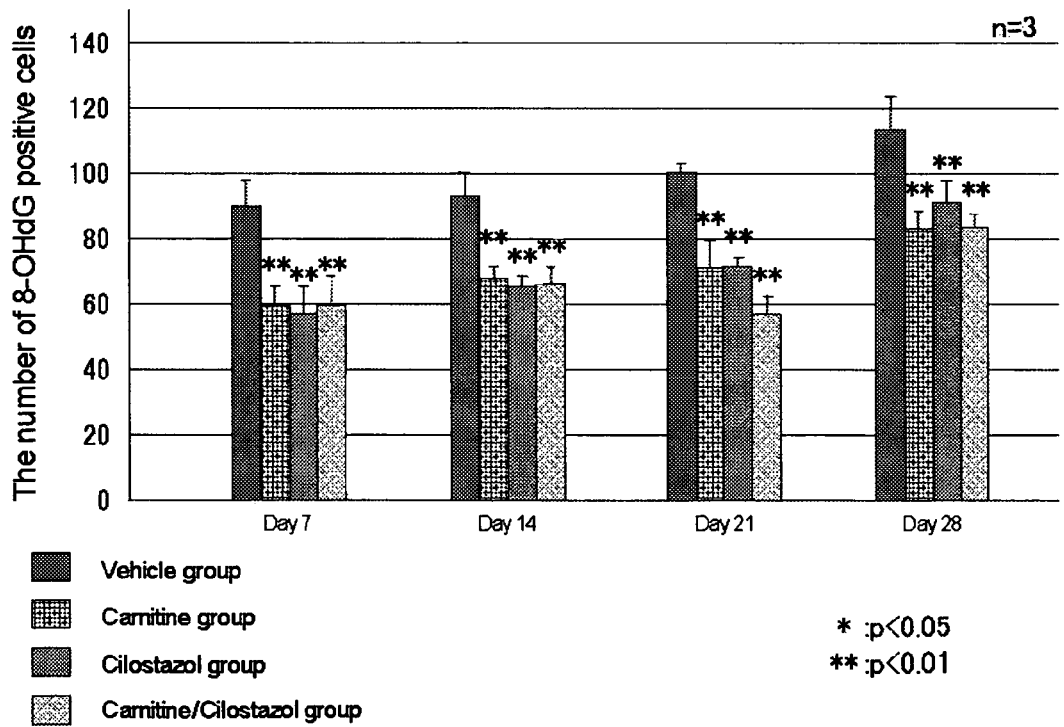
FIG. 3 shows the time-dependent change of the number of 8-OHdG positive cells (8-OHdG staining) in each group.

As shown in FIG. 3, 8-hydroxydeoxyguanosine (8-OHdG) positive cell which indicates cell dysfunction by peroxidation tended to time-dependently increase in the vehicle group from day 7 to day 28 after LBCCA, while every positive cell in the carnitine group, the cilostazol group, and the carnitine/cilostazol combination group significantly decreased (P<0.01).

Figure 4:
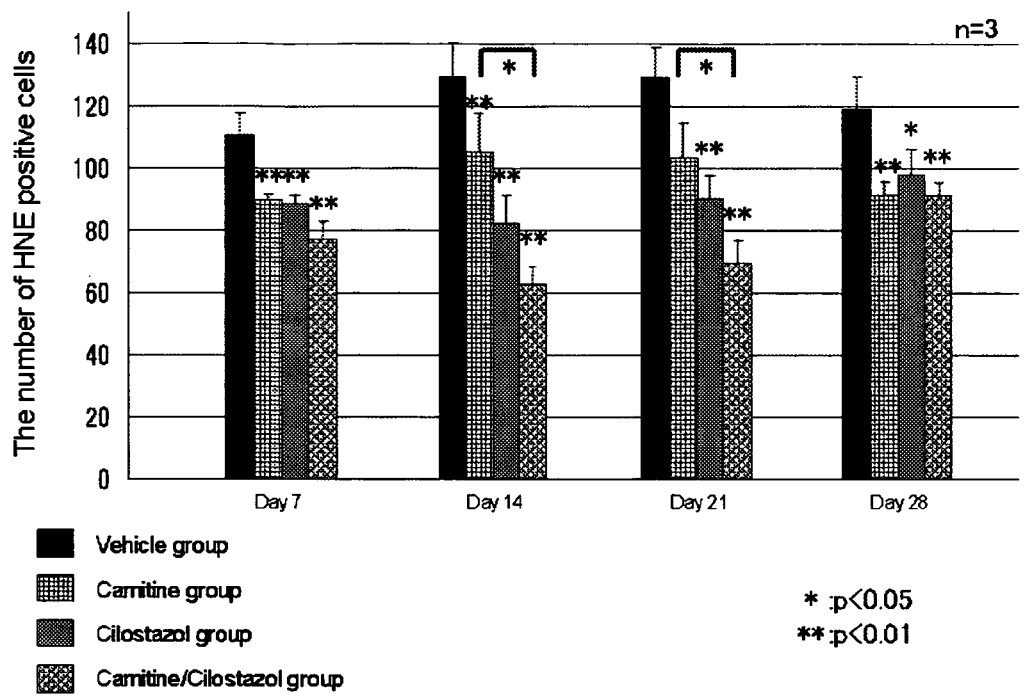
FIG. 4 shows the time-dependent change of the number of HNE positive cells (HNE staining) in each group.

As shown in FIG. 4, in the HNE staining which indicates the yield of peroxidative metabolism, the positive cells of the carnitine group, cilostazol group; and the carnitine/cilostazol combination group tended to significantly decrease compared with the vehicle group (P<0.01). On days 14 and 21, the carnitine/cilostazol combination group exhibited a lower value than the carnitine group (P<0.05).

Figure 5:
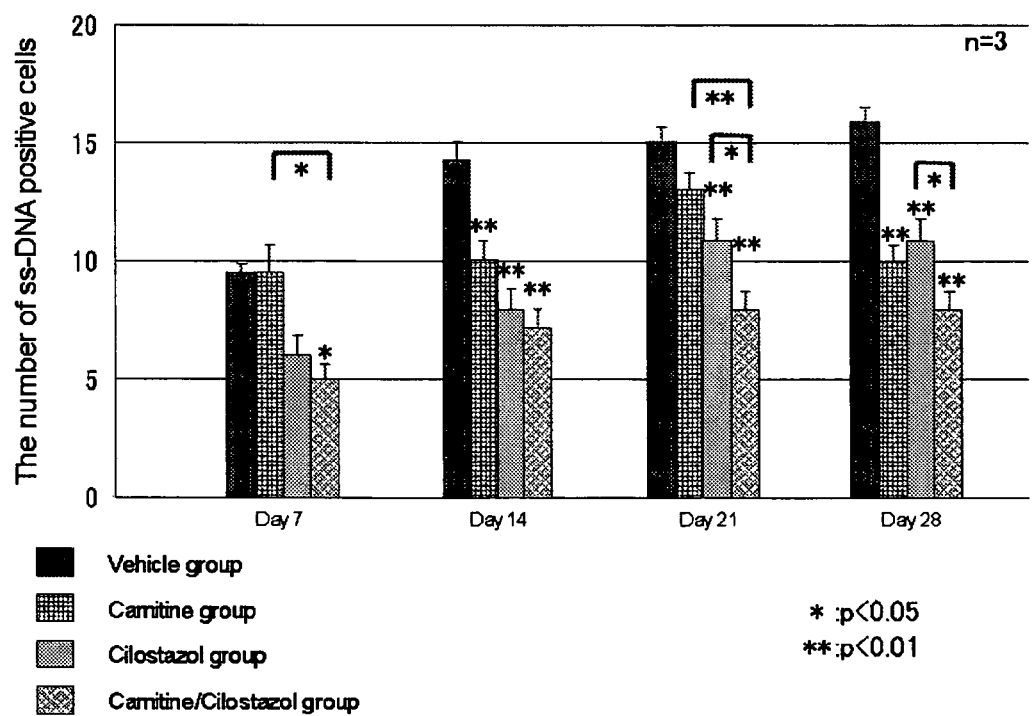
FIG. 5 shows the time-dependent change of the number of ss-DNA positive cells (ss-DNA staining) in each group.

FIG. 5 shows the results of ss-DNA staining as a marker of apoptosis. As for the staining of the carnitine group on day 14, the staining of the cilostazol group on days 14, 21 and 28, and the staining of the carnitine/cilostazol group on days 7, 14, 21 and 28, the number of the positive cells significantly decreased compared with the vehicle group (P<0.01). Further, regarding the comparison between the groups, the cell count of the carnitine/cilostazol combination group decreased on days 7 and 21 compared with the carnitine group, and additionally decreased on days 21 and 28 compared with the cilostazol group (P<0.05).

The invention claimed is:

1. A method for treating occlusive peripheral arterial disease comprising administering to a patient in need thereof a therapeutically effective amount of a combination comprising as active ingredients 6-[4-(1-cyclohexyl-1H-tetrazol-5-yl)butoxyl]-3,4-dihydrocarbostyril or a salt thereof; and carnitine or a salt thereof; in a ratio of 0.1 to 100 parts by weight of carnitine or a salt thereof per 1 part by weight of the carbostyril derivative or a salt thereof.

2. The method of claim 1, wherein the occlusive peripheral arterial disease is acute arterial occlusive disease, thromboangiitis obliterans, arteriosclerosis obliterans, lumbar spinal stenosis, or intermittent claudication.

3. The method of claim 2 wherein the occlusive peripheral arterial disease is intermittent claudication.

4. The method of claim 3, wherein the ratio is 1-20 parts by weight of carnitine or a salt thereof per 1 part by weight of 6-[4-(1-cyclohexyl-1H-tetrazol-5-yl)butoxy]-3,4-dihydrocarbostyril or a salt thereof.

* * * * *